US00PP08031P

United States Patent [19]

Laver

[11] Patent Number: Plant 8,031

[45] Date of Patent: Nov. 17, 1992

[54] MINIATURE ROSE PLANT NAMED LAVQUEST

[75] Inventor: Keith Laver, Caledon East, Canada

[73] Assignee: Springwood Consultants, Ltd., Ontario, Canada

[21] Appl. No.: 674,515

[22] Filed: Mar. 22, 1991

[51] Int. Cl.[5] ..... A01H 5/00

[52] U.S. Cl. ..... Plt./9

[58] Field of Search ..... Plt./7, 7.1, 9

*Primary Examiner*—Howard J. Locker

*Attorney, Agent, or Firm*—Christie, Parker & Hale

[57] ABSTRACT

A new miniature rose plant producing light pink flowers.

1 Drawing Sheet

SUMMARY OF THE INVENTION

The present invention relates to a new and distinct variety of rose plant of the miniature rose class, which was originated by my crossing as seed parent the variety known as 'Loving Touch' and as pollen parent the variety known as 'Ontario Celebration'. The varietal denomination of this new rose is 'Lavquest'.

Among the novel characteristics possessed by this new variety which primarily distinguish it from its parents and all other varieties of which I am aware are its ease of propagation from softwood cuttings, dwarf compact habit, soft pink flower color, good shelf-life and resistance to powdery mildew.

Lavquest is particularly suited for commercial pot rose production for 4-inch or 5-inch pots because of its ease of rooting from softwood cuttings, uniform flowering habit, long flower life on the plant and bloom production in short periods.

Asexual reproduction by propagation of softwood cuttings of the new variety as performed in Somis, Calif. shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DETAILED DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart.

Parentage: Seedling.

*Seed parent.*—'Loving Touch'.

*Pollen parent.*—'Ontario Celebration'.

Class: Miniature.

The following observations are made of specimens grown in a greenhouse environment in Somis, Calif., during the period of Oct. to Jan.

FLOWER

Blooming Habit: Continuous.

A. Bud:

(1) *Size.*—$\frac{3}{8}$th inch when the petals start to unfurl.

(2) *Form.*—Pointed ovoid.

(3) *Color.*—When sepals first divide, near 49D; When half blown, the upper sides of the petals are near 49D intensifying to near 48B at the center of the flower and the undersides of the petals are the same.

(4) *Sepals.*—Color—near 138A. Surface texture—covered in fine hairs. There are normally three appendaged sepals and two unappendaged sepals with hairy edges.

(5) *Receptacle.*—Color— near 138A. Shape— funnel. Size— small (3/16"×3/16"). Surface — smooth.

(6) *Peduncle.*—Length — short (about 1"). Surface — smooth. Color — medium green. Strength — stiff, erect, slender.

B. Bloom:

(1) *Size.*—Small, average open size is $1\frac{1}{2}$ inches.

(2) *Borne.*—Singly and several together, in flat clusters.

(3) *Stems.*—Short, strong.

(4) *Form.*—When first open — high center, becoming flat. Permanence — retains its form to the end, outer petals curl back with some quilling.

(5) *Petalage.*—Number of petals under normal conditions — about 45 to 50.

(6) *Color.*—The upper side of the petals is near 49B for center petals and near 49D for other petals. The reverse side of the petals is the same as upper side. The base of the petals is small green half moon at point of attachment (about $\frac{1}{4}$"×$\frac{1}{4}$"). The major color on the upper side is near 49C to D. No change in color at the end of the first day; fading on outer petals to near 49D at the end of the third day.

(7) *Fragrance.*—Slight.

C. Petals:

(1) *Texture.*—Thin.

(2) *Shape.*—Deltoid.

(3) *Form.*—Tips slightly recurved, edges slightly quilled.

(4) *Arrangement.*—Imbricated (regularly arranged, shingle-like).

(5) *Petaloids in center.*—Few.

(6) *Persistence.*—Hand on and dry.

(8) *Lasting Quality.*—On the plant — Long (5–7 days).

REPRODUCTIVE ORGANS

A. Anthers:
*Size.—medium, many.*
*Color.—yellow.*
*Arrangement.*—Regularly arranged around syles.

B. Filaments:
*Color.*—Yellow.

C. Pollen:
*Color.*—Lemon yellow.

D. Styles:
*Color.*—Greenish white.

E. Stigmas:
*Color.*—Red.

PLANT

Form: Bush.

B. Growth: Vigorous, dwarf, upright, branching, compact.

C. Foliage:
(1) *Size.*—Small; about 2″ long × 1½″ wide.
(2) *Quantity.*—Normal.
(3) *Color.*—New foliage — light green. Old foliage — dark green.

D. Leaflets:

(1) *Number of leaflets on normal mid-stem leaves-*.—5, occasionally 7.
(2) *Shape.*—Pointed oval.
(3) *Texture.*—Upper side — smooth.
(4) *Edge.*—Serrate.
(5) *Serration.*—Single.
(6) *Petiole rachis Color.*—Green.
(7) *Petiole underside.*—Rough, with prickles.
(8) *Stipules.*—Short (¼″), bearded.
(9) *Resistance to Disease.*—Resistance to mildew.

E. Wood:
*New wood.*—Color — light green. Bark — smooth.
(2) *Old wood.*—Color — green. Bark — smooth.

F. Prickles:
(1) *Quantity.*—On main canes from base — ordinary. On laterals from main canes — ordinary.
(2) *Form.*—Long, medium, hooked downward.
(3) *Color when young.*—Red.

G. Small Prickles:
*On main stalks.*—None.
*On laterals.*—None.

I claim:

1. A new and distinct variety of rose plant of the miniature rose class, substantially as shown and described.

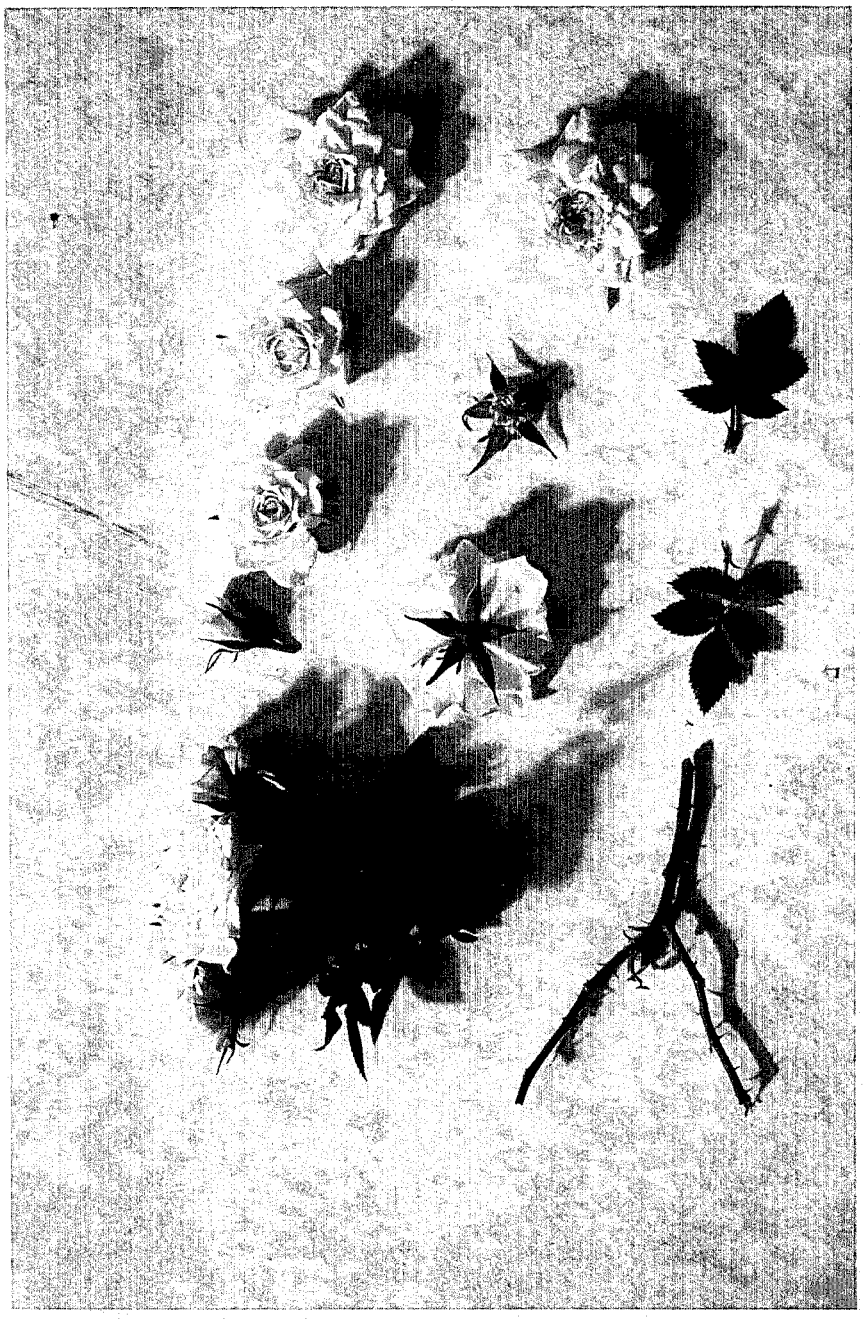

* * * * *